United States Patent [19]

Heiba et al.

[11] 4,190,588

[45] Feb. 26, 1980

[54] METHOD OF PREPARING A SUBSTITUTED BUTYROLACTONE ACETIC ACID

[75] Inventors: El-Ahmadi I. Heiba, Princeton; Albert L. Williams, Hopewell Township, Mercer County, both of N.J.

[73] Assignee: Mobil Oil Corporation, New York, N.Y.

[21] Appl. No.: 618,173

[22] Filed: Sep. 30, 1975

Related U.S. Application Data

[63] Continuation-in-part of Ser. No. 355,360, Apr. 27, 1973, Pat. No. 3,925,232, which is a continuation-in-part of Ser. No. 212,626, Dec. 27, 1971, abandoned.

[51] Int. Cl.$^2$ ............................................ C07D 307/32
[52] U.S. Cl. .......................... 260/343.6; 260/326.25; 260/429.9; 252/153; 252/355; 252/542; 252/544; 252/545; 252/546; 260/326.45
[58] Field of Search ........................................ 260/343.6

[56] References Cited

U.S. PATENT DOCUMENTS

| | | | |
|---|---|---|---|
| 3,155,685 | 11/1964 | Prill et al. | 260/343.5 |
| 3,936,472 | 2/1976 | Kinney et al. | 260/343.6 |

*Primary Examiner*—Alan L. Rotman
*Assistant Examiner*—Natalia Harkaway
*Attorney, Agent, or Firm*—Charles A. Huggett; Vincent J. Frilette

[57] ABSTRACT

Metal salts and amides of alkyl-lactam acetic acids are prepared by reacting gamma-hydrocarbyl butyrolactone acetic acid compounds derived from alkenylsuccinic anhydrides with metal compounds and amines or amines alone. High molecular weight lactam acid salts and amides and metal complexes and metal carbamates thereof are useful as detergents or dispersants in organic industrial fluids. Another aspect of this invention is a method of preparing lactone acetic acids in yields up to 90% conversion from alkenylsuccinic anhydrides.

4 Claims, No Drawings

METHOD OF PREPARING A SUBSTITUTED BUTYROLACTONE ACETIC ACID

CROSS REFERENCE TO RELATED APPLICATIONS

This application is a continuation-in-part of U.S. application Ser. No. 355,360, filed Apr. 27, 1973, now U.S. Pat. No. 3,925,232, which, in turn, is a continuation-in-part of U.S. application Ser. No. 212,626, filed Dec. 27, 1971, now abandoned.

BACKGROUND OF THE INVENTION

1. Field of the Invention

This invention relates to metal salts or amides and metal or amide lactones and lactams for use as hard water soaps and organic fluid additives. In particular, this invention relates to soaps and amides of lactone acetic acids derived from alkenylsuccinic anhydrides.

2. Description of the Prior Art

In an article of D. D. Phillips and A. W. Johnson (*Journal of the American Chemical Society*, Vol. 77, page 5977, 1955), there is described a reaction of allylic-substituted succinic anhydride with 6 normal hydrochloric acid. This article does not disclose reaction of the lactone acetic acid with an alkali metal and an amine.

In U.S. Pat. Nos. 3,200,075 and 3,261,782 there are described the preparations of esters and amides of alkyl butyrolactone acetic acids which are obtained by reacting an olefin with di-methyl bromosuccinate. However, the final products of this patent are not the same as those prepared in accordance with the present invention.

SUMMARY OF THE INVENTION

We have discovered that organo-substituted lactone acetic acids or their esters or thioesters derived from alkenylsuccinic anhydrides may be reacted with (a) an alkali metal compound and an amine in either order or (b) an amine to produce two types of products:

(1) a metal or amine salt or amide of 3-amidocarbonyl or 3-metallocarboxy-5-hydroxycarboxylic acid, and (2) a metal salt or amide of a butyrolactam acetic acid. The lower molecular weight carboxylates of Type 1 are extremely effective as hard water soaps or detergents. The higher molecular weight lactam acetic acid salts or amides of Type 2 or their metal complexes or carbamates are useful as organic industrial fluid dispersants or detergents.

DESCRIPTION OF SPECIFIC EMBODIMENTS

In accordance with this invention, organo-substituted gamma-lactone acetic acid may be obtained by subjecting alkenylsuccinic anhydrides to acid hydrolysis. The preparation of the anhydrides is known (U.S. Pat. Nos. 2,568,876 and 3,219,666). Essentially, this preparation involves the reaction between a 1-olefin and maleic anhydride (or halosuccinic or succinate ester). It is understood that one effect of this reaction involves predominantly a shift of the unsaturated bond of the olefin to produce the alkenylsuccinic anhydride

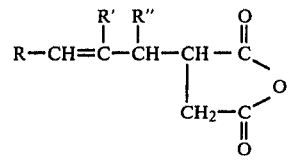

wherein R, R' and R" each may be hydrogen or hydrocarbyl of 1 to about 300 carbon atoms. Hereinafter the terms "Type 1" and "Type 2" will be used to refer to both the final products or to the alkenylsuccinic anhydrides and the lactone intermediates from which the products are derived.

Normal olefins (R' and R" are hydrogen) and branched olefins (R" is hydrogen) may produce

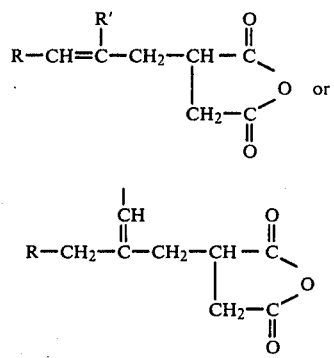

wherein the dangling valence represents the remainder of R'. In each of these cases at least one of the unsaturated carbon atoms is in the main chain of the alkenyl group and the carbon atom adjacent to the succinyl group contains two hydrogen atoms. The lactone acetic acid produced from these anhydrides (Type 1) is a gamma-hydrocarbyl-gamma-butyrolactone acetic acid. Controlled reaction with an alkali metal compound or amine leads to the metal or amine, i.e. organoammonium salt of the lactone acid. Heating the amine salt to remove water would produce amide of the lactone acid. Further reaction of the metal or amine salt or amide with an amine produces the corresponding 3-amidocarbonyl-5-hydroxycarboxylate. The amide of the lactone acid may also be reacted with a metal salt to produce the amide of 3-metallocarboxy-5-hydroxycarboxylate. At least one of R and R' is alkyl containing from 1 to about 30 carbon atoms, and more preferably one is alkyl of 5 to 25 carbon atoms and the other hydrogen. These carboxylates are excellent hard water soaps, containing metal and amido groups in the same molecule.

However, higher molecular weight alkenylsuccinic anhydrides derived from olefin polymers, such as polyisobutylene, may have a number of side chains as in the following illustrative structure

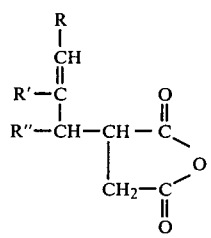

wherein R'' is hydrocarbyl. The resulting lactone acetic acids made from such anhydrides (Type 2) are understood to consist of at least a large, if not predominant, portion of beta-hydrocarbyl-gamma-butyrolactone acetic acid. Initial reaction with alkali metal compound or amine produces the corresponding lactone acid salt or amide. We have found that further reaction with amine can be carried out at high temperature, but analysis of the resulting product reveals the presence substantially of the lactam acetate salt or amide. It is noted that commercially available olefin polymers and the alkenylsuccinic anhydrides obtained therefrom may consist of mixtures which include various type of interlinking. Hence, some ring-opening reaction may occur in the same reaction mixture. It is contemplated, therefore, that some 5-hydroxycarboxylate products may be present in the final product mixture.

The various reaction products of this invention will be discussed in more detail subsequently.

In one aspect of this invention, an alkenylsuccinic anhydride is reacted with a mineral acid in the presence of water, preferably under reflux conditions. This hydrolytic reaction yields the corresponding lactone acetic acid and from 40% to 50% by weight of alkenylsuccinic acid. It is unexpectedly discovered that if the reaction mixture is treated with an inert organic solvent, such as toluene, and distilled, the solvent, water and acid may be withdrawn, leaving the lactone acetic acid component untouched, while the alkenylsuccinic acid is converted back to the alkenylsuccinic anhydride. The anhydride is further treated with acid and water to yield a new reaction mixture containing over 80% of the desired lactone acetic acid. A second distillation with solvent followed by the acid-water treatment produces a reaction mixture containing at least 90% by weight of the lactone acetic acid.

Hydrochloric acid and toluene are the preferred acid and solvent in this reaction sequence because they permit water to be removed conveniently as an azeotrope with the toluene. Other solvents include benzene, xylene and the like. A 6-normal hydrochloric acid concentration is preferred. A typical reaction between hydrochloric acid and succinic anhydride in the presence of water is understood to proceed as follows:

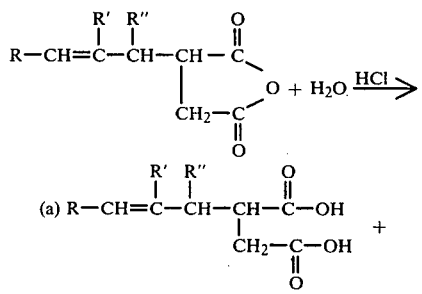

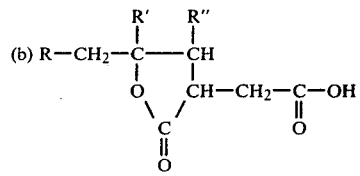

wherein R, R' and R'' have the aforesaid definitions.

A modification of this process involves reacting the alkenylsuccinic anhydride with an alcohol or mercaptan in the presence of an acid-acting catalyst. This process is disclosed and claimed in U.S. application Ser. No. 324,939, filed on Jan. 19, 1973, Pat. No. 3,936,472. The resulting product is an ester or thioester of the lactone acetic acid,

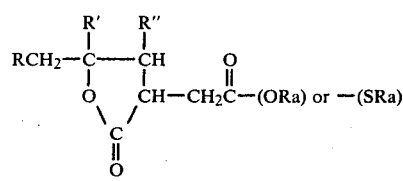

$R_a$ being the organic portion of the alcohol or thiol, of 1 to 20 carbon atoms, preferably 1 to 6. This mode of preparation is preferred because the anhydride is converted to a lactone acid compound in only one step at 90% or more yield. The ester or thioester may be reacted directly with an amine to produce the lactone amide; alternatively each may be hydrolyzed back to the lactone acid for further reaction with the alkali metal compound.

Preferred alcohols in this process are the lower aliphatic monohydric alcohols of from 1 to 6 carbon atoms. Methanol is particularly convenient to employ. Also useful are ethanol, propanol, butanol, pentanol, and such thiols as methyl mercaptan, ethyl mercaptan, and the like. Heterogeneous catalysts useful in this process include the preferred ion-exchange resins having acid groups attached. Sulfonic acid groups attached to a vinyl or vinyl-copolymer matrix provide a very effective catalyst. Mineral acids, such as hydrochloric, other sulfonic acids, such as p-toluenesulfonic, are also suitable.

Type 1 Products

The lactone acetic acid or ester or thioester derived from the Type 1 alkenylsuccinic anhydride is reacted with an alkali metal compound or an amine which does not open the lactone ring. A strong alkali, such as sodium hydroxide, could open the lactone ring. The resulting di-sodium soap, while having soap properties, can be precipitated in hard water by calcium or magnesium. Therefore, one of the preferred Type 1 products of this invention is that in which an amine is reacted with the lactone acid first to produce a lactone amine salt, or a lactone amide. Then a strong alkali, preferably sodium hydroxide or other alkali hydroxides, may then be reacted with the intermediate to open the ring, thereby placing a metallocarboxy group at the 3-carbon of the carboxylate, as in

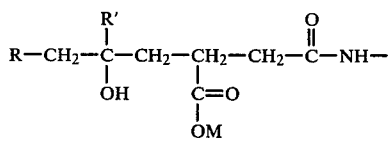

wherein the dangling valence is the remainder of the amine reactant and M is the alkali metal. Products of this type possess very good utility as aqueous detergents.

Also of importance in this invention are those products in which the metal or amine salt or amide is prepared initially, followed by opening the ring with an amine instead of the metal reactant. The alkali metal compound is preferred as the initial reactant in this modification. The most suitable alkali reactants include alkali metal carbonates and bicarbonates, for example sodium bicarbonate, sodium carbonate, potassium bicarbonate, potassium carbonate, lithium carbonate and the like; also the metal hydrides, such as lithium hydride. The alkali metal neutralizes the acetic acid portion of the molecule without opening the ring of the lactone. This reaction may be carried out in the presence of a polar solvent such as water, mono- and polyhydric alcohols and ethers of from about 1 to 6 carbon atoms, such as methanol, ethanol, propanol and dimethoxyethane, inert hydrocarbons, such as toluene or benzene, also tetrahydrofuran and mixtures thereof. Lithium hydride is preferably used in tetrahydrofuran. A water-methanol mixture also provides a satisfactory solvent system. The resulting mono-metal salts of the gamma-lactone acid have cleaning properties and form suds in water, although they are also precipitated by calcium.

The amines also useful in this phase of the reaction sequence, include both primary and secondary alkyl amines, cycloalkyl amines and aralkyl amines, ethylenepolyamines, and alkanolamines and ethoxylated (pre-reacted with ethylene oxide) alkanolamines. The amine reactants may have from 1 to about 20 carbon atoms and from 1 to about 10 nitrogen atoms.

The gamma-lactone acetic acid soaps or amides are understood to have the following structure:

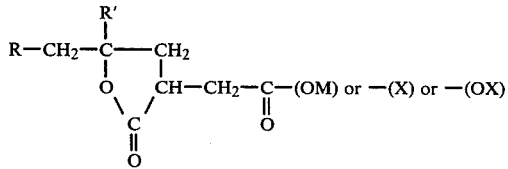

wherein R and R' may each be hydrogen or alkyl of from 1 to about 30 carbon atoms, and M is an alkali metal, (OX) is the substituted ammonium of the amine reactant and X is the amino group —N< of the amine reactant.

These soaps or amides are then reacted with an amine. The lactone ring opens and the carbonyl group of the lactone forms an amide with the amine.

The amines useful in this second step of our invention may be any amine having an —NH— group, such as alkyl, cycloaklyl, aralkyl and the like of from 1 to about 20 carbon atoms, including methyl amine, ethyl amine, diethyl amine, propyl amine, dipropyl amine, hexyl amine, dodecyl amine, cyclohexyl amine, benzyl amine and polyamines, particularly ethylene polyamines, such as ethylene diamine, diethylene triamine, triethylene tetramine and tetraethylene pentamine. This second amine may be the same as that used in the preceding step. Of particular interest are the alkanolamines, such as diethanolamine and monoethanolamine which is the most preferred reactant for preparing aqueous soaps and detergents. This second reaction can be carried out in the presence of any solvent as used in the previous reaction or in a nonpolar solvent depending upon the reaction temperature desired. The reaction mixture may be refluxed at temperatures ranging from over room temperature, about 30° C., to 250° C., preferably up to about 175° C. Reaction with monoethanolamine permits an equimolar reaction, i.e. 1 mole of amine per mole of metal salt, or amine salt.

It is understood that Type 1 product of this reaction sequence is a 5-hydroxy carboxylate, having the general structure:

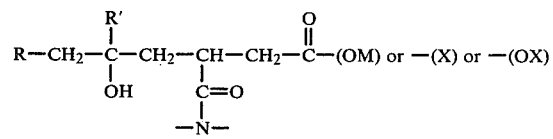

wherein M and X have the previous definitions and the dangling valences are the remainder of the amine reactant. One of the most preferred compounds of Type 1 is

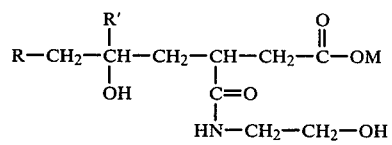

wherein R is alkyl of 5 to 25 carbon atoms, R' is hydrogen, and M is sodium. The metal hydroxyamides are so effective in hard water that they are not precipitated by the presence of high concentrations of calcium or magnesium.

The preferred reaction product may be further reacted with ethylene oxide to produce ethoxylated derivatives. Ether groups are added onto the ethanolamine portion of the molecule and provide additional hydrophilic properties to the soap. From 1 to 20 moles of ethylene oxide per mole of hydroxyamide soap may be added. The reaction may be carried out at low temperatures, using a liquefied ethylene oxide feed. The ethanolamine reactant may also be pre-ethoxylated before reaction with the metal lactone acid soap.

Type 2 Products

The second class of products of this invention are useful in organic industrial fluids, such as lubricating oils, greases, fuels, transmission fluids and the like. The alkenyl portion of the succinic anhydride from which they are derived is obtained from olefin polymers, preferably derived from propylenes, butylenes, amylenes, hexenes and the like. One or any combination of R, R' and R" may be hydrocarbyl of from 25 to 800 carbon atoms. Preferably, the total carbon atom content of the alkenyl group may range from 30 to about 300 carbon atoms, and the different R-groups are alkyl.

As discussed previously, unbranched long-chained hydrocarbon olefin polymers used in preparing the alkenylsuccinic anhydride precursor are not readily obtainable, and moreover, they may produce waxy products. High molecular weight olefins suitable for making organic fluid additives are often branched, such as polyisobutylene. Although this Type 2 alkenylsuccinic anhydride may be converted to the lactone acid or ester or thioester (as the Type 1 anhydride), we have found that the lactone ring is not readily opened by subsequent reaction with amines or alkalis to produce the 5-hydroxycarboxylate products of Type 1.

The preferred products of this aspect of our invention are those in which the lactone acid or ester is reacted with an amine having at least one —$NH_2$ group at a temperature of from 125° to about 300° C., and preferably from 175° to 275° C., to yield a lactam amide believed to have the structure

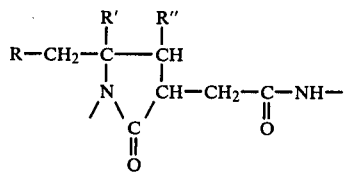

wherein R, R' and R" may be hydrogen or hydrocarbyl, R" preferably being alkyl, the total R, R' and R" containing from about 30 to about 800 carbon atoms and the dangling valences being the remainder of the amine reactant. Different amines may be used to form the amide group and the lactam group, e.g. a polyamine for the amide and a monoamine for the lactam ring.

The preferred amine reactant used in preparing dispersants or detergents for organic compositions is alkylene polyamine of the formula $H_2N—(C_mH_{2m}NH)_n—H$, wherein m is an integer of 2 to 4 and n is an integer of 1 to 10, preferably 1 to 6. Preferably, m is 2, and the amines are ethylene diamine, diethylene triamine, triethylene tetramine, tetraethylene pentamine, pentaethylene hexamine and the like. However, monoamines may be used of from 1 to about 30 carbon atoms, such as the alkyl amines, methyl amine, ethyl amine, butyl amine, cyclohexyl amine, etc., and aralkyl amines, e.g. benzyl amine.

When the preferred polyamines are used, the final reaction product may contain the above structures and polymers thereof, poly(lactam)amido molecules having up to over 3,000 carbon atoms. If P stands for the divalent polyamino group —$(C_mH_{2m}NH)_{n-1}—C_mH_{2m}—$, LA stands for a divalent lactam amido

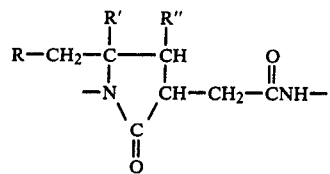

and AL stands for a divalent amido lactam

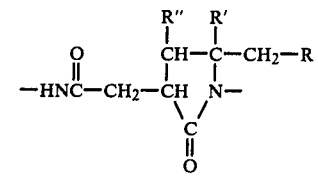

then the following products may occur in the reaction mixtures of this invention: -P-LA-P-AL-, -P-LA-P-LA-, -P-AL-P-LA-, -P-AL-P-AL-, -P-AL-P-LA-P-AL-P-AL-, -P-LA-P-LA-P-AL- and the like. The lactone amides of polyamines may also interact under the conditions of this invention to produce bis(lactam)amides. If the same amine is used to form both the amide and the lactam, the addition of amine to lactone acid or ester may be carried out in a single step. Both lactone and lactam amides are useful in the organic compositions of this invention.

The metal lactam acid salts may also be prepared by reacting the lactone acid with the alkali metal compound, followed by reaction with the amine. Using tetraethylene pentamine as the amine and a sodium salt of the lactone acid for illustration, the reaction products may have the structures

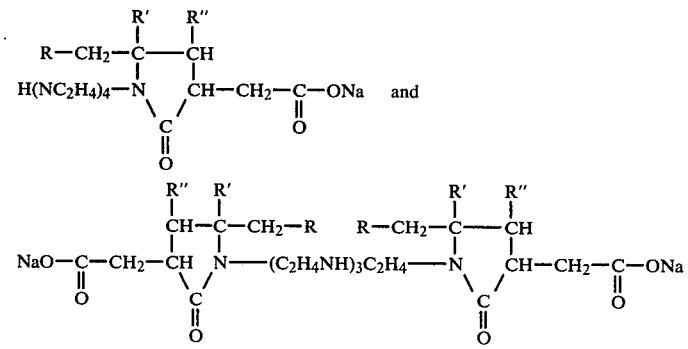

These high molecular weight monomeric and polymeric lactone and lactam products and the above salts also have detergent and dispersant properties in lubricating oils and other organic fluids. The preferred amine for the preparation of high molecular weight bis(lactone)amides and lactam amides, as indicated above, is tetraethylene pentamine. The preferred polyolefin used in the formation of the succinic anhydride is polyisobutylene or polybutene. Alkaline earth metal salts are also useful detergents.

We have further discovered that the lactone and lactam amides can be reacted with a metal salt of an alcohol or phenol and carbon dioxide to form a metal carbamate with any basic nitrogen atom remaining in the molecule. Alkali or alkaline earth metal alkoxides or phenates, such as sodium, potassium, calcium, barium and the like salts are suitable reactants. The preferred alcohols contain from 1 to about 20 carbon atoms. Simple alcohols, such as methanol, propanol, butanol, t-butanol, amyl alcohol, hexanol and the like may be used. Phenol or $C_1$-to $C_{20}$-alkylphenol are also satisfactory sources for the metal salt. Of interest are the overbased salts in which the metal, preferably alkaline earth metal, is present in a greater concentration than stoichiometric. Preparations of such over-based phenates are well known, such as described in U.S. Pat. Nos. 3,350,310 and 3,036,971. The metal salt and the lactam or lactone amide are mixed together in the presence of carbon dioxide under moderate heat or at room temperature for a sufficient period of time to effect reaction.

It is understood that any terminal or internal nitrogen atom on the polyamine can enter the carbamate reaction, as for example

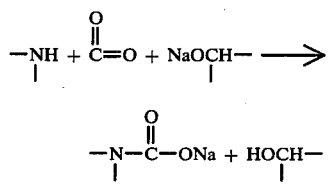

These carbamates have utility as oil or gasoline dispersants or detergents.

We have also discovered that the lactone and lactam amide products of this invention may form complexes with metal compounds, particularly with the metals of Groups Ib, IIb or VIII of the Periodic Table, such as zinc. Of particular interest are zinc salts of organic acids and phenates, such as zinc carboxylates of 1 to 20 carbon atoms, zinc methane sulfonate, zinc hydroquinones, and zinc phenates. Alkyl-substituted phenates and hydroquinones may also be used, in which the alkyl groups contain from 1 to about 25 carbon atoms. The complexes may be prepared by adding the zinc salt to the reaction mixture containing the lactone or lactam amide or the amide may be blended into the organic medium, such as a lubricating oil, first and then the zinc salt is added. The amide and salt are heated slightly under agitation until solution is obtained.

The following examples are provided for the purpose of illustrating the various aspects of this invention.

EXAMPLE 1

A one-liter flask is fitted with a magnetic stirrer and a reflux condenser, and 153 g of n-hexadecenyl succinic anhydride (0.475 mole) are introduced. To this is added 200 ml of 6 N. hydrochloric acid. The mixture is stirred and brought to reflux. The reaction mixture is held at reflux for 17 hours. Then 150 ml of toluene are added, and the water and hydrochloric acid are distilled from the system by means of a Dean-Stark trap to convert by-product diacid back to anhydride. Distillation is continued to take off the toluene. The Dean-Stark trap is then removed and the 200 ml of 6 N. hydrochloric acid replaced in the flask. Again the mixture is refluxed with stirring for 17 hours. The 150 ml of toluene is added back, and the dilute acid again distilled off. Treatment with 6 N. hydrochloric acid is repeated in this way for two more times. The toluene is distilled off leaving 161 g. of gamma-n-tetradecylgamma-butyrolactone-2-acetic acid. Infrared spectra show the purity to be 90%.

EXAMPLE 2

A solution of 50 g of gamma-n-decyl-gamma-butyrolactone-2-acetic acid (0.176 mole) is prepared in a one liter round bottom flask containing 500 ml of dry tetrahydrofuran at 25° C. The flask is fitted with a stirrer, condenser, and gas inlet tube. To this is added 1.40 g of lithium hydride (0.176 mole) under nitrogen. The mixture is stirred and brought to reflux. The mixture is heated at reflux for 40 hours. To this is then added 16.2 g of ethanolamine (0.264 mole) and refluxing under nitrogen is continued for 22 hours. A small amount of white insoluble solid is removed by filtration. The product is recovered from the filtrate by evaporation of solvent and excess amine by using a bath at 90° C. and pressure down to 1 mm Hg in a rotary evaporator. The yield of lithium 3-hydroxyethylamido-5-hydroxypentadecanoate is 52 g.

EXAMPLE 3

A solution of 14.0 g of gamma-n-decyl-gamma-butyrolactone-2-acetic acid (0.0493 mole) is prepared in 200 ml of refluxing methanol in a 500 ml round bottom flask fitted with a condenser. A solution of 4.57 g of sodium bicarbonate (0.0542 mole) is prepared in a beaker containing 30 ml of water at 65° C. The hot bicarbonate solution is poured slowly into the refluxing solution of lactone-acid in methanol. The mixture is refluxed for ten minutes after the addition is made. Methanol and water are then removed in a rotary evaporator. The sodium salt residue is dissolved in 100 ml of refluxing tetrahydrofuran in a 500 ml round bottom flask, fitted with a reflux condenser, to give a cloudy solution. The heat is turned down to stop refluxing, and to the solution is added 3.00 g of ethanolamine (0.0490 mole). The mixture is then reheated to reflux under a nitrogen atmosphere. The reaction mixture is held at reflux for 45 hours. After cooling to room temperature, the solution is filtered to remove a small amount of white solid. Removal of the tetrahydrofuran from the filtrate by rotary evaporation leaves 15.3 g of sodium 3-hydroxyethylamido-5-hydroxypentadecanoate.

EXAMPLE 4

By the method of example 3 a monosodium salt is prepared by the reaction of gamma-n-tetradecyl-gamma-butyrolactone-2-acetic acid (16.7 g) with sodium bicarbonate (5.0 g). The crude sodium salt (0.049 mole) is heated and stirred with 100 ml of tetrahydrofuran. After cooling to 30° C. it is filtered free of suspended white solid. The filtrate is transferred to a 300 ml round bottom flask and solvent is evaporated off to leave 50 ml of solution. To the solution of the sodium salt is added 3.00 g of ethanolamine (0.0490 mole). The mixture is then refluxed for 72 hours under nitrogen. Removal of the solvent by rotary evaporation gives a yield of 20 g of sodium 3-hydroxyethylamido-5-hydroxynonadecanoate.

EXAMPLE 5

Gamma-n-tetradecyl-gamma-butyrolactone-2-acetic acid (10.0 g) (29.4 millimoles) is dissolved in 10 ml of dry tetrahydrofuran in a 200 ml flask by heating and stirring. To this solution are added 4.5 g (73.5 millimoles) of ethanolamine. The flask is fitted with a reflux condenser and the mixture is brought to reflux for three hours. Solvent and excess ethanolamine are evaporated off at 1 mm of mercury pressure to leave a yield of 13.6 g of 2-hydroxyethylammonium 3-hydroxyethylamido-5-hydroxynonadecanoate.

EXAMPLE 6

A solution of 102 g of alkyl-gamma-butyrolactone-2-acetic acid (0.049 mole) is prepared in 500 ml of tetrahydrofuran. The acid was obtained by reacting polyisobutylene having a molecular weight of about 900 (about 64 carbon atoms) with maleic anhydride and treating the resulting alkenylsuccinic anhydride in a manner similar to Example 1. The solution is then treated with 1.0 g of lithium hydride (0.124 mole), as in Example 2. After 63 hours at reflux the excess lithium hydride is filtered off. Removal of the tetrahydrofuran from the filtrate by rotary evaporation leaves 102 g mixture of lithium beta-alkyl- and gamma-alkyl-gamma-butyrolactone-2-acetate. The flux the excess lithium hydride is filtered off. Removal of the tetrahydrofuran from the filtrate by rotary evaporation leaves 102 g mixture of lithium beta-alkyl- and gamma-alkyl-gamma-butyrolactone-2-acetate. The 1° C. with stirring for 18 hours. The product is then blown with a stream of nitrogen for 2 hours at 240° C. to yield 51 g of bis(lithium beta-alkyl-gamma-alkyl-gamma-butyrolactam-2-acetate) of tetraethylene pentamine.

EXAMPLE 7

A 200 ml round bottom flask is fitted with a reflux condenser, nitrogen inlet tube, thermometer and magnetic stirrer. There are then introduced 30.0 g (0.014 mole) of the lactone acid used in Example 6 and 2.65 g (0.014 mole) of tetraethylene pentamine. The mixture is stirred and heated under nitrogen at 240° C. for 24 hours. The flask is then flushed with nitrogen for 1 hour, and then cooled to yield 32 g of a reaction mixture containing a polymeric amido-lactam believed to have the structure

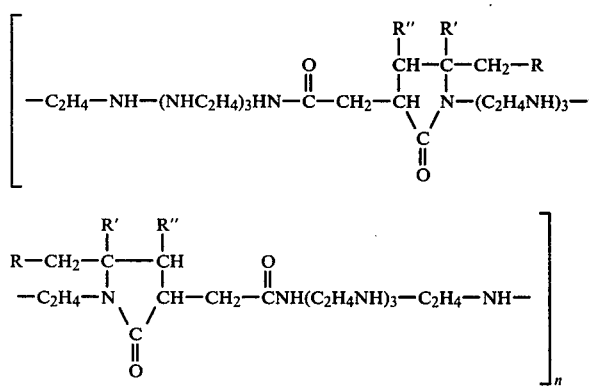

R, R', R' together having about 64 carbon atoms, n being at least one Infrared analysis of this product shows a band at 1650–1680 cm$^{-1}$ due to the amide carbonyl group, and a band at 1700 cm$^{-1}$ due to the lactam carbonyl group.

It should be noted that reaction between the lactone acid and an amine (as opposed to the alkali metal compound) would normally produce the substituted ammonium salt. However, under high temperature conditions, the amide forms at the acetic acid portion of the molecule. Also, there may be both simpler as well as more complicated polymeric molecules in the reaction mixture.

EXAMPLE 8

Into a 5-liter flask fitted with a reflux condenser, stirrer and thermometer were added 1220 grams of a product of a reaction between polyisobutene of about 1300 molecular weight (about 93 carbon atoms) and maleic anhydride. About 700 grams (0.5 mole) of the added amount is the succinic anhydride, the remainder being unreacted polyisobutene. To the flask were added 1200 ml of n-octane with moderate heating (to about 50° C.) and agitation to form a solution, followed by 46 grams (1.5 mole) of methanol and 150 grams of an ion exchange resin of sulfonic acid on a vinyl-divinylbenzene copolymer matrix in bead form. The mixture was heated to reflux with stirring for 12 hours. The resulting solution was separated from the beads and filtered.

Atmospheric distillation of the solution took off 32 grams of methanol and the n-octane. The remaining 1236 grams consists of the 520 grams of polyisobutene and about 716 grams of the methyl ester of the corresponding lactone acetic acid. Infrared spectra shows about 90% gamma-butyrolactone ester and about 10% of a delta-lactone ester.

EXAMPLE 9

Into a 500-ml flask were added 100 g (0.34 mole) of n-tetradecenylsuccinic anhydride, 16.3 grams (0.51) of methanol and 250 ml of n-octane. The reaction mixture was heated to reflux at about 70° C. with stirring. The temperature rose to 80° C. and maintained at that level for two hours. Octane and excess methanol were stripped off leaving 105 grams of the half methyl ester of n-tetradecenylsuccinic acid.

In a sealed glass pressure vessel, containing 47 grams of the said half ester, 15 grams of the sulfonic acid resin catalyst of Example 8, 50 ml of n-octane and 10 drops of methanol, the reaction mixture was stirred and heated at 125° C. for three hours. The mixture was then cooled, diluted with ethanol and the catalyst filtered off. Ethanol and octane were evaporated leaving 41.6 grams of the methyl ester of the corresponding lactone acid.

This ester is hydrolyzed with hydrochloric acid and the resulting lactone acid is reacted in the same manner as in Example 4 to produce the sodium 3-hydroxyethylamido-5-hydroxyheptadecanoic acid.

EXAMPLE 10

Into a 4-necked flask fitted with a Dean-Stark trap under a condenser, thermometer, stirrer and nitrogen inlet tube are added 1620 grams of a reaction product prepared in a manner similar to that of Example 8, of which about 58% by weight is the methyl ester of the alkyl-gamma-butyrolactone acetic acid (0.648 mole) and the remainder is polyisobutene, and 122.7 grams (0.648 mole) of tetraethylenepentamine. The reactor is swept with nitrogen and sealed under a nitrogen atmosphere. The contents of the flask are stirred and heated to 140° C. After 4 hours at this temperature, the temperature was raised to 220° C. while methanol was collected in the trap. The mixture was held at this temperature for 20 hours. The yield of resulting reaction product is 1720 grams.

EXAMPLE 11

Using equipment and procedure similar to that of Example 10, a mixture was prepared consisting of 747 grams of a reaction product (1) prepared in a manner similar to that of Example 8 except that the alkyl groups on the lactone ring contain about 64 carbon atoms, of which product about 81% by weight is the methyl ester of the alkyl-gamma-butyrolactone acetic acid (0.575 mole) and the remainder is polybutene, and 851 grams of a reaction product (2) prepared as in Example 8 except the alkyl groups on the lactone ring contain about 190 carbon atoms, of which product about 47.5% by weight is the methyl ester (0.144 mole), to which mixture were added 136 grams (0.719 mole) of tetraethylenepentamine. The reaction mixture was heated at 140° C. under nitrogen for 4 hours and at 220° C. for 20 hours with stirring. The yield of resulting reaction mixture was 1710 grams.

EXAMPLE 12

Zinc complexes were prepared by mixing the lactamamide prepared in a manner similar to that of Example 10 into a mineral lubricating oil blend at a concentration of about 5% by weight. The oil blend was heated to about 60° C. with stirring and the zinc salt was added in sufficient amount to provide a particular concentration of zinc. The salts used were (a) monozinc di-(dodecyl)-hydroquinone, (b) dizinc 2,2'-methylenebis(6-octadecylhydroquinone) and (c) monozinc tri(octadecyl) phenol.

EVALUATION OF PRODUCTS

The lower molecular soaps of this invention are tested in very hard water in which the water hardness, calculated as parts per million of calcium carbonate is 450. The soap is added at a concentration of 0.4% by weight. The products of examples 2 and 3 are tested as well as the sodium soap of a $C_{19}$ acid (sodium 3-hydroxyethylamido-5-hydroxy-nonadecanoate). None of the soaps tested results in precipitation of calcium. A similar test is carried out using the same soap concentration with an ordinary sodium palmitate. Upon mixing, the calcium soap precipitates and no suds are obtained. Sodium palmitate soap is mixed with the product of Example 3, the concentrations being 0.3% by weight of the hydroxyamide soap and 0.2% by weight of sodium palmitate. This mixture is precipitated in the hard water. However, the precipitate remains dispersed for over 3 hours.

The washing properties and resistance to precipitation in hard water of the products of this invention, even in absence of conventional builders and sequestrants, are demonstrated in a series of washing tests. The tests are made in a Terg-O-Tometer Model 7243, manufactured by United States Testing Company, Inc. of Hoboken, N.J., using a test procedure essentially as recommended by United States Testing. Several soaps are used by adding various amounts to a liter of water having a hardness of at least 100 ppm. as $CaCO_3$. Soiled cloths with an average reflectance of 67% are cleaned by essentially the following procedure: the cloth is placed in a 2-liter stainless steel beaker with the sample soap solution at about 120° F. and agitated by an impeller at 110 cycles per minute for 15 minutes; the cloths are rinsed in the same hard water for from 2 to 5 minutes. After drying the cloths are measured for reflectance in a reflectance meter which reads percent of reflected light, using magnesium oxide as 100% reflectance. The increased reflectances of the cleaned cloths are as follows:

| Soap | Conc., % bw | Increased Refl., % |
|---|---|---|
| FMPA 101 COTTON CLOTHS | | |
| Product of Example 2 | 0.02 | 7 |
|  | 0.04 | 9.7 |
| Product of Example 4 | 0.02 | 8 |
|  | 0.04 | 12.8 |
| DACRON/COTTON CLOTH | | |
| Product of Example 4 | 0.02 | 8.8 |
|  | 0.04 | 18.2 |

Several soaps are tested in this test in the presence of other additives, as follows: 15% soap, 5% sodium silicate, 39.5% sodium tripolyphosphate, 39.5% sodium sulfate and 1% sodium carboxymethyl cellulose. The product of example 4 provided an increased reflectance for Dacron/cotton cloths of 25% and for EMPA 101 cotton of 32%. A sodium 3-hydroxyethylamino-5-hydroxy-$C_{21}$ carboxylate, in this formulation, provided an increased reflectance for Dacron/cotton cloths of 25% and for EMPA 101 cotton of 31%.

In a simulated washing test, 200 ml of hard water ($CaCl_2$ at 450 ppm calculated as $CaCO_3$) is placed in a rectangular porcelin wash bowl (with plunger drain) of 14 in. × 10½ in. × 7 in. deep (at plunger). Then 200 ml of $H_2O$ containing 300 mg of a soap is poured in. The hardness is now 225 ppm as $CaCo_3$. The water is gently stirred with a microspatula for 2 minutes, then allowed to stand for 3 minutes. The plunger is raised to permit the water to drain over 1 minute. After another minute, the bowl is wiped dry with a pre-dried tared paper towel.

The paper towels used in this test are first wetted with distilled water and dried in an oven at 75° C. for 1½ hours, then weighed and allowed to cool at room temperature for 1 hour. The towels are again weighed. All weighings are done in a tared 250 ml beaker. The moisture in the atmosphere provided an increase in weight of 7 mg.

The soaps used in the test are the product of example 4 and sodium stearate. If precipitates form in the bowl during mild agitation, the weight of the towel after wiping the bowl would be increased. The following results are obtained:

| Soap | Weight Gain, mg |
|---|---|
| Blank | 7 (atmospheric moisture) |
| Example 4 product | 11 |

| Soap | Weight Gain, mg |
|---|---|
| Sodium Stearate | 69 |

The following test shows the ability of the high molecular weight lactams of this invention to maintain particulate solids in oils in suspension.

(a) In a stainless steel cylindrical cell mounted in a constant temperature bath of 100° C., 1 g of nickel powder is formed in a porous bed on a 400-mesh nickel screen, and 5 cc of a white oil is passed through to set the powder and fill the spaces of the cell bed. Then, 10 cc of the white oil solution containing 2% by weight of a dispersant and 250 ppm of carbon black (0.18 micron diameter) dispersed therein is passed through the bed at 1cc/min. Light transmission measurements of the mineral oil-dispersion are made before and after the passage through the bed to determine the amount of dispersed carbon adhering to the nickel bed (Beer-Lambert law is applicable).

(b) A modification of this procedure involves depositing carbon black on the bed separately by passing 10 cc of a dispersion of 250 ppm of the carbon black in white oil through the bed at 1 cc/min. followed by 5 cc of white oil alone. Then the white oil-additive solution is passed through at 1cc/min. Again, this solution has been measured before and after for light transmission. The percent of light transmission is proportional to the amount of carbon present.

Products of Ex. 7 and 10 are compared with a bisalkenylsuccinimide wherein the alkenyl group has a formula weight of about 900. The following results are obtained, as percent reduction of carbon black:

| Dispersant | (a) Deposit Avoidancy | (b) Deposit Removed |
|---|---|---|
| None | 10 | 0 |
| Alkenylsuccinimide | 50 | 22 |
| Example 7 | 90 | 24 |
| Example 10 | — | 45 |

The higher the percent of carbon black retained or picked up, the more effective the dispersant. (Preparation of carbon black dispersions in both tests involve mixing 12.5 mg of 0.18 micron diameter carbon black in 50 grams of the detergent solution or white oil alone and subjecting the mixture to ultrasonic radiation at 80 KC/sec for 15 minutes.)

The zinc complexes of lactam amides as prepared in Example 12 were also tested in the carbon removal test. The same procedure for preparing those complexes were used for complexing the above bis-alkenylsuccinimide for the purpose of comparison, using the same base oil stock in each comparison. The concentration of the nitrogen-containing material, 5%, was used for the lactam-amide and the succinimide. The results were as follows:

| Detergent, 5% | Zinc Salt | Zinc Conc. in Oil, (% by wt.) | Deposit Removed, % |
|---|---|---|---|
| Example 12 Product | (a) | 0.062 | 48 |
| Succinimide | (a) | 0.062 | 25 |
| Example 12 Product | (b) | 0.021 | 37 |
| Succinimide | (b) | 0.021 | 21 |
| Example 12 Product | (c) | 0.062 | 24 |
| Succinimide | (c) | 0.062 | 17 |

EXAMPLE 13

Into a pressure bottle was added a solution consisting of 25 ml of dry t-butyl alcohol and 64 grams (14.08 m-moles) of bis(gamma-alkyl-butyrolactone) amide of tetraethylene pentamine (7.04 m-moles of amine), the alkyl group being derived from a polybutene having a molecular weight of about 1300. Into this solution was mixed a solution of sodium t-butoxide in t-butyl alcohol prepared by dissolving 0.324 gram (14.08 m-moles) of sodium in 275 ml of t-butyl alcohol with stirring overnight in a closed flask. The pressure bottle containing the mixture is flushed with carbon dioxide and pressurized with $CO_2$ to 20 psig.

The reaction mixture was stirred at room temperature for 24 hours. The t-butyl alcohol was removed, leaving 64.8 grams of thick liquid product. Infrared spectrum shows the product to be a lactone (5.67 microns)-amide (6.0 microns)-carbamate (6.35 microns).

EXAMPLE 14

A solution of 10 grams (4.2 m-moles) of a lactam amide of tetraethylene pentamine (4.2 m-moles of the amine), the alkyl substituent on the ring having a molecular weight of 1300, and 50 ml of n-octane was added to a pressure bottle. To this solution was added 1.85 grams of overbased calcium phenate containing 4.2 m moles of calcium (or 9.1% Ca) in 10 ml of n-octane. The pressure bottle was flushed with carbon dioxide and pressurized to 20 psig with $CO_2$.

The mixture was stirred at room temperature for 24 hours. The octane was removed under vacuum. The remaining product of 12.0 grams was shown by infrared analysis to be a lactam (5.88 microns)-amide (6.0 microns)-carbamate (6.35 microns).

The products of Examples 13 and 14 were evaluated in the carbon removal test described previously. A 5% solution of carbamate in white oil was passed through the bed of carbon black (10 cc at 1 cc/min.). The results for each product and the oil alone were as follows:

| Dispersant | Carbon Removed, % |
|---|---|
| None | 0 |
| Example 13 | 16 |
| Example 14 | 20 |

The products of this invention may be used as hard water soaps, or additives for industrial organic fluids. These soaps are useful both alone or in the presence of known, conventional soap additives, builders or perfumes and the like. The low molecular metal or ammonium salts of the 3-amido-5-hydroxy carboxylates may be used not only in water, but they are also useful as detergents or dispersants in organic fluids, such as gasoline, light machine oils and the like. As gasoline additives, R groups of from 10 to about 30 carbon atoms could be used. The higher molecular weight products, mostly lactone amides, lactam amides, bis-lactams, or interlinked polymeric or macro-molecular products find utility as detergents or dispersants in mineral oils.

Having described our invention, we claim:

1. The method of preparing a butyrolactone acetic acid having the structure

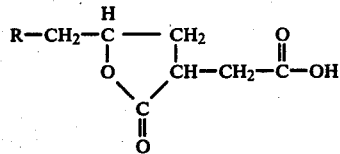

wherein R is hydrogen or hydrocarbyl of 1 to about 300 carbon atoms, said method comprising the steps of (1) reacting an alkenyl succinic anhydride, wherein the first and second carbon atoms attached to the succinyl group are unbranched, with a mineral acid in the presence of water thereby forming a reaction mixture of said butyrolactone acetic acid and by-product alkenyl succinic diacid, (2) treating said reaction mixture with an inert organic solvent and distilling, thereby withdrawing said solvent, said mineral acid and water from said reaction mixture and converting said by-product alkenyl succinic diacid to anhydride, and (3) subsequently treating the mixture of said butyrolactone acetic acid and alkenyl succinic anhydride with mineral acid in the presence of water thereby increasing the butyrolactone acetic acid content of said mixture.

2. The method described in claim 1 wherein said mineral acid is hydrochloric acid and said inert organic solvent is toluene.

3. The method described in claim 1 wherein said alkenyl succinic anhydride is n-hexadecenyl succinic anhydride.

4. The method described in claim 1 wherein said steps (2) and (3) are repeated, thereby further increasing the butyrolactone acetic acid content of said mixture.

* * * * *